(12) United States Patent
Prause

(10) Patent No.: US 6,945,112 B2
(45) Date of Patent: Sep. 20, 2005

(54) TESTING DEVICE FOR THE ULTRASONIC INSPECTION OF BARSTOCK

(75) Inventor: Reinhard Prause, St. Augustin (DE)

(73) Assignee: GE Inspection Technologies Systems GmbH (DE)

( * ) Notice: Subject to any disclaimer, the term of this patent is extended or adjusted under 35 U.S.C. 154(b) by 165 days.

(21) Appl. No.: 10/474,468

(22) PCT Filed: Dec. 7, 2001

(86) PCT No.: PCT/DE01/04600

§ 371 (c)(1),
(2), (4) Date: Oct. 9, 2003

(87) PCT Pub. No.: WO02/084274

PCT Pub. Date: Oct. 24, 2002

(65) Prior Publication Data

US 2004/0103722 A1 Jun. 3, 2004

(30) Foreign Application Priority Data

Apr. 11, 2001 (DE) .......................... 101 18 124

(51) Int. Cl.⁷ ............................................ G01L 29/04
(52) U.S. Cl. ....................................................... 73/622
(58) Field of Search .......................... 73/622, 620, 623, 73/644

(56) References Cited

U.S. PATENT DOCUMENTS 3,107,521 A * 10/1963 McClure ...................... 73/640
3,358,497 A * 12/1967 Hank ........................... 73/49.1
3,838,609 A * 10/1974 Denkowski et al. .......... 74/625
3,877,293 A * 4/1975 McKeage ..................... 73/49.1
4,189,944 A * 2/1980 Day et al. ..................... 73/623
5,085,783 A * 2/1992 Feke et al. .................. 210/748

FOREIGN PATENT DOCUMENTS

DE 199 31 350 A1 12/2000

* cited by examiner

*Primary Examiner*—Hezron Williams
*Assistant Examiner*—Jacques M. Saint-Surin
(74) *Attorney, Agent, or Firm*—Akerman Senterfitt

(57) ABSTRACT

The invention relates to a testing device for ultrasonic bar (30) testing, comprising a container (20) a) with a chamber disposed therein where the ultrasonic testing is carried out which b) is provided with at least one through-passage (28) for bars which are to be tested and which c) has at least one inlet and at least one outlet for a coupling fluid (52), especially water, whereby the inlet and outlet are arranged in such a way the coupling fluid (52) is circulated around the bar (30) in a cross-wise direction in relation to the longitudinal direction thereof (32), in addition to comprising at least one ultrasonic test head (46) which is directed at the bars (30). The chamber has a non-circular cross-section perpendicular to the longitudinal direction (32) of the bars (30) and the cross-section of the chamber is adapted to the profile of the bars (30) in such a way that the width of a gap (42) running between the bars (30) and the wall (40) of the chamber is substantially maintained.

11 Claims, 3 Drawing Sheets

TESTING DEVICE FOR THE ULTRASONIC INSPECTION OF BARSTOCK

Figure 1:
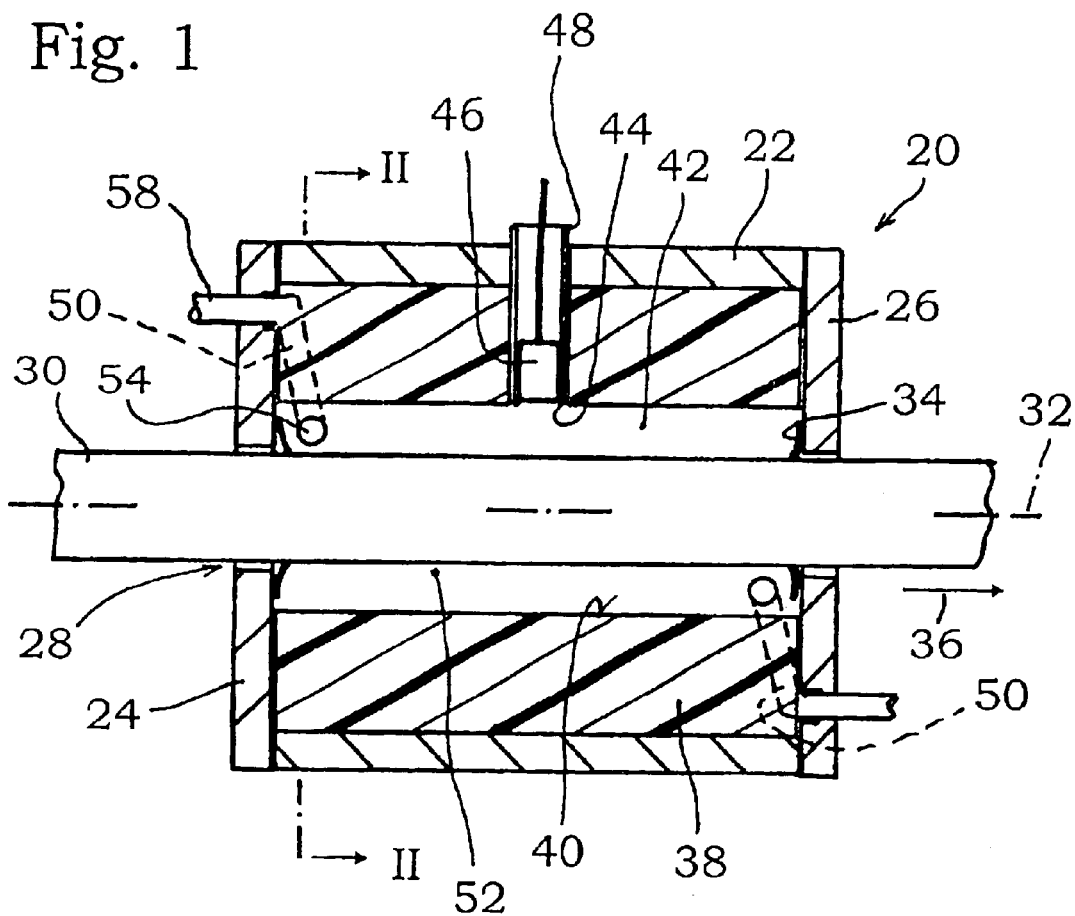

The invention relates to a testing device for the ultrasonic inspection of barstock with
a container a) having a chamber disposed therein in which the ultrasonic inspection is carried out, b) being provided with at least one passage for barstock to be inspected and c) being comprised of at least one inlet and at least one outlet for a coupling fluid, more specifically water, inlet and outlet being arranged in such a manner that in operation the coupling fluid is circulated around the barstock in a direction transverse to the longitudinal direction thereof and with at least one ultrasonic probe that is pointed at the barstock.

A testing device of the type mentioned herein above has been previously known from DE 199 31 350 A. The previously known testing device has a tubular container with a substantially cylindrical inner volume with a round cross-section transverse to the longitudinal direction of the barstock. This inner volume forms the chamber in which ultrasonic inspection takes place.

Said previously known testing device has been found very efficient for testing substantially round barstock. If however the barstock to be tested has an angular section, like flat, square, hexagonal and so on stock material, problems arise during ultrasonic inspection.

Looking closer at the problems, it has been found that the fluid is poorly circulated around angular stock materials. The greater their departure from a round section, the poorer the fluid circulation around them. As a result, trailing edges, bubbles and so on will form. These interfere with ultrasonic inspection.

This is where the invention comes in. Its object is to develop the testing device of the type mentioned herein above in such a manner that it is also suited for testing angular stock material, meaning also for barstock the section of which greatly departs from a round cross-section.

In view of the testing device of the type mentioned herein above, the solution to this object is that the chamber has a non round cross-section in a direction transverse to the longitudinal direction of the barstock and that the cross-section of the chamber is matched to the section of the barstock in such a manner that a perimeter gap between barstock and inner wall of the chamber substantially maintains its width.

In this testing device, the chamber in which the ultrasonic testing takes place is no longer the same for every testing task and for every barstock to be tested, it is rather matched to the section of the barstock to be tested. A container, more specifically a jacket of the container, that is matched to the respective barstock may be used for the purpose. It is however more specifically suggested to provide adapter inserts that are insertable into the inner volume of the container and that match the size and shape of the inner volume to the section of the barstock to be tested in such a manner that a perimeter gap between barstock and inner wall of the chamber will not substantially change in width. It has been found that a variation in width of the gap over the perimeter of less than 3:1, preferably of less than 2:1 is sufficient.

In matching the chamber to the respective barstock, selective and controlled circulation of the fluid around said barstock is achieved. The problems heretofore known using chambers with a circular cross-section may thus be avoided. Even bars the section of which greatly departs from the round cross-sectional shape may thus be inspected. Even flat stock material may be readily tested.

During inspection it is known to move the barstock relative to the container and, as a result thereof, relative to the at least one ultrasonic probe which is stationary with respect to the container. By thus moving the barstock to be inspected, different areas thereof are scanned one after the other. In suitably arranging a plurality of ultrasonic probes, it is achieved that the section of the barstock is sufficiently inspected, meaning the respective testing task is performed.

In order to allow the barstock to move relative to the container, the container has at least one passage for the barstock to be inspected and preferably has two passages placed opposite each other in the longitudinal direction. These are also matched to the respective barstock to be inspected. They accordingly have a shape that conforms to the section of the barstock. They additionally have seals that come into, if possible sealing, contact with the surface of the barstock.

In principle, it is possible to additionally rotate the barstock about its longitudinal axis when it is moved through the container. It is however preferred that the barstock be passed through the container without being rotated. In this case, the necessary ultrasonic tests are achieved by a sufficient number of probes that are distributed about the section of the barstock and perform the various respective testing tasks in a profile cross-section.

The coupling fluid used is substantially water, but any other fluid such as oil may be used in principle. The coupling fluid may be reused as often as desired, it may be circulated in a circuit. At need, a filter is inserted into the circuit for retaining dirt particles and so on which are carried along with the fluid. The circuit is actuated by a pump for example. The device may also be operated without circulation. In this case, water is drawn under pressure from a supply line and is flown through the testing device prior to being evacuated.

Figure 2:
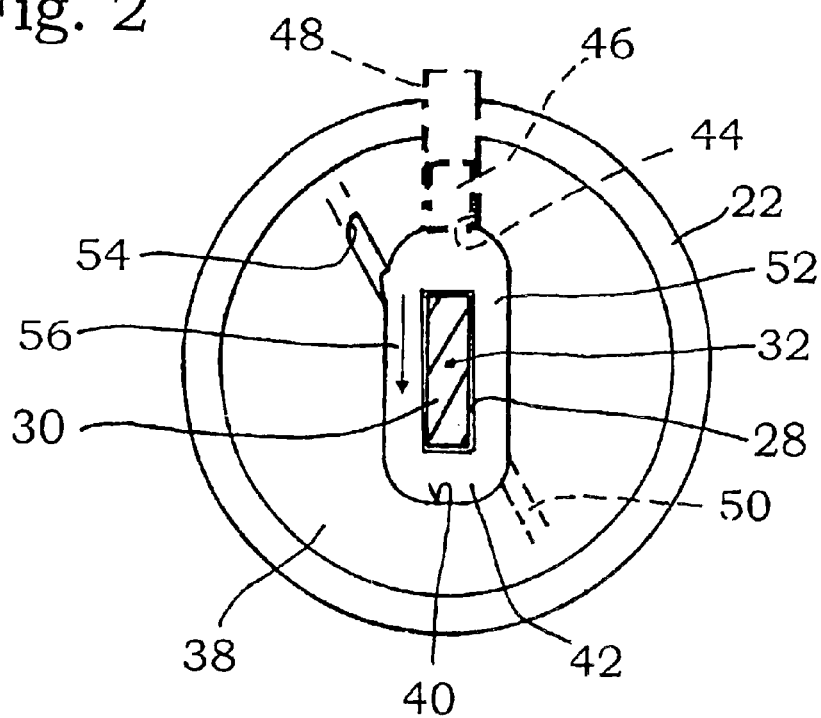
Figure 3:
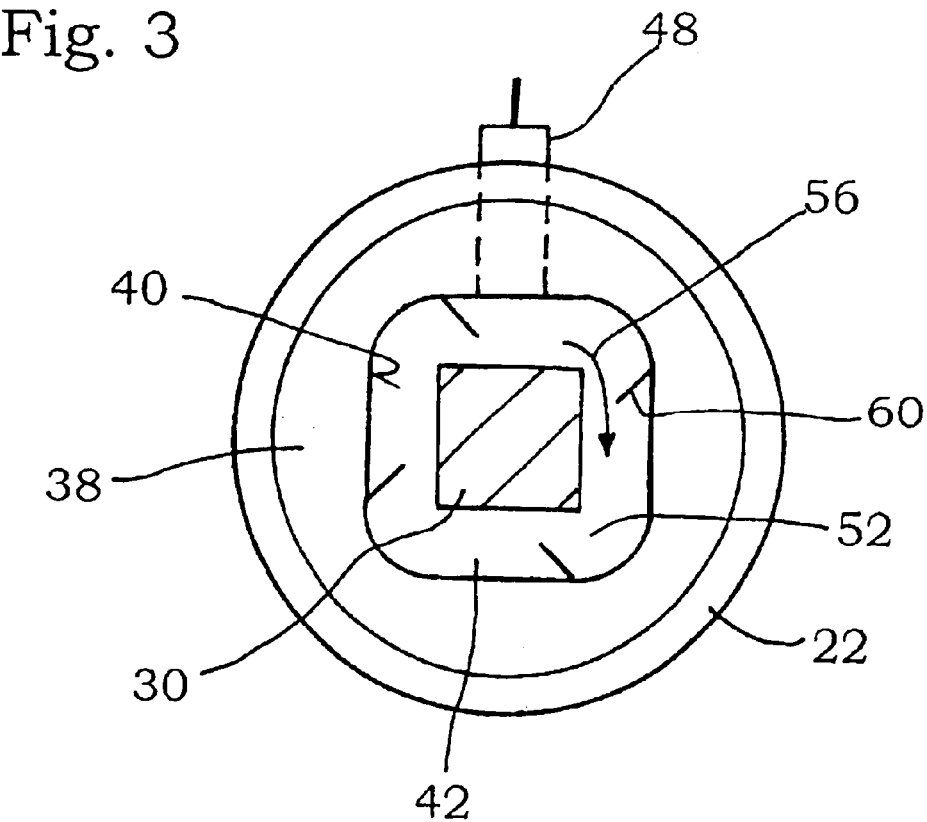
Figure 4:
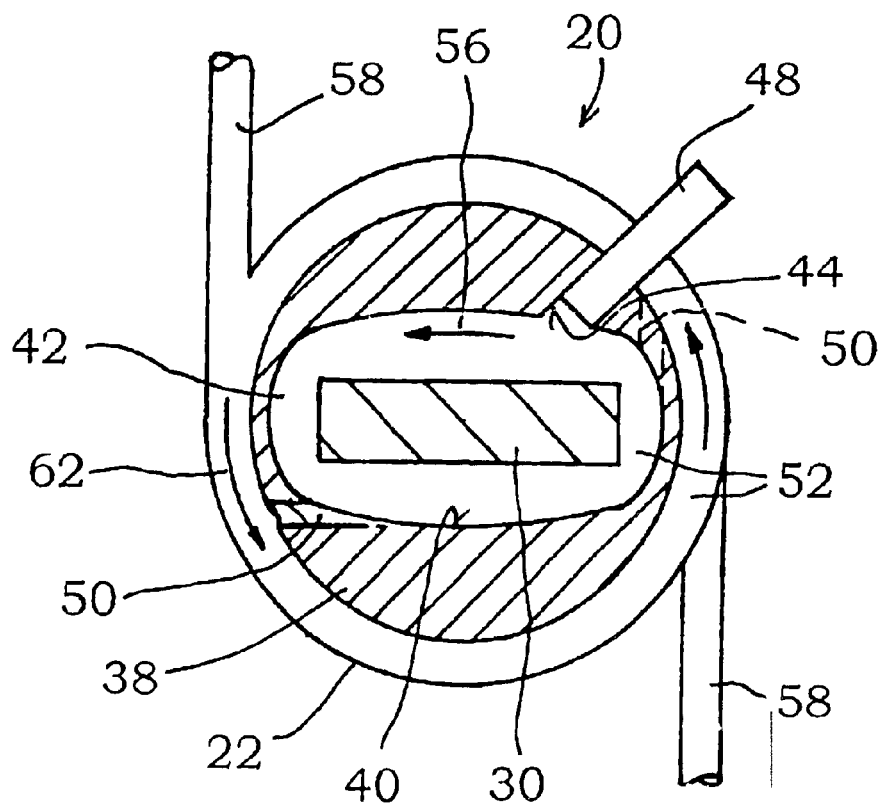
Figure 5:
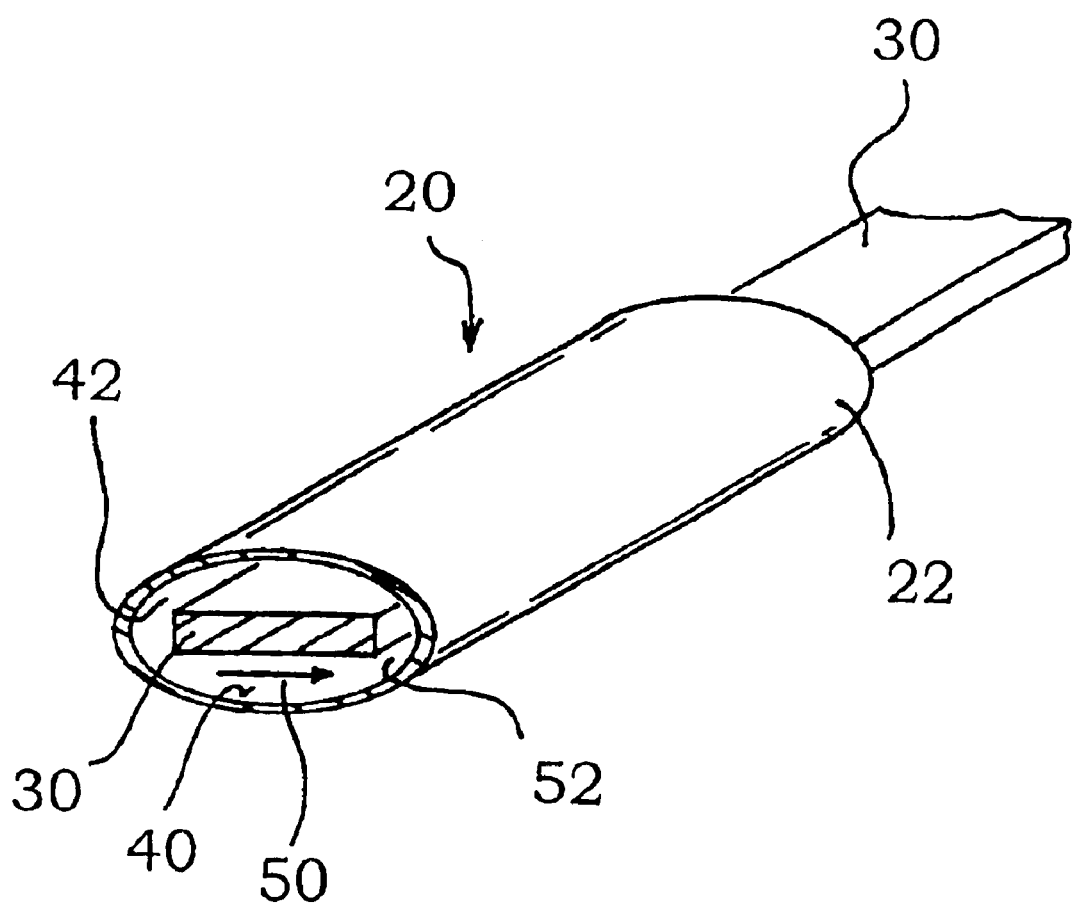

Further advantages and characteristics of the invention will become apparent in the claims and in the following non restrictive description of embodiments thereof, given by way of example only with reference to the drawings in which:

FIG. 1: is a lengthwise sectional view of a testing device and of an inspected barstock that is passed through said testing device, FIG. 2: is a sectional view taken along line II—II of FIG. 1, FIG. 3: is a sectional view like FIG. 2, but now for a barstock having a square section and with another adapter insert than in FIG. 1 and FIG. 2, FIG. 4: is a sectional view similar to FIG. 2 with an adapter insert that has a cylindrical runner on the outer wall thereof, and FIG. 5: is a perspectively designed cross-section of a testing device with a non round jacket.

The testing device for the ultrasonic inspection of barstock has a container 20 that, in the exemplary embodiments shown, is comprised of an jacket 22 and of two end walls 24, 26. In principle, such a structure is not compulsory. The container may be of any shape and configuration.

In the exemplary embodiment shown, the end walls 24, 26 are built according to the same principle. They each have a passage 28 that is disposed in the center thereof. Said passage allows the barstock 30 to be inspected to be introduced into, and withdrawn from, the container 20. The barstock has a longitudinal direction 32. Said direction is oriented on the line of the centroid of the cross-sectional area of barstock 30.

In the configuration shown, the jacket 22 is a cylindrical jacket. Other jacket shapes such as square jackets may be used in principle. The end walls 24, 26 are matched to the jacket. In the embodiment shown, circular disks have been assembled to form a seal with the border of the cylindrical jacket 22.

They may be detached from the jacket 22 to laterally expose the full cross-section of the jacket. The end walls 24, 26 are preferably composed of two portions as has been disclosed in the above mentioned DE 199 31 350.

The end walls 24, 26 may be readily replaced. Various sets of end walls 24, 26 are provided. Different end walls 24, 26 are provided for a respective profile cross-section of the barstock 30 to be inspected. They differ in the shape of the passage 28. Said passage 28 is matched to the section of the barstock 30 to be inspected. It has seals 34 that are arranged in such a manner that they ride along the surface of the barstock when said barstock is moved through the testing device in the direction of arrow 36. It is possible and there is provided that an end wall be configured with a greater central opening and that different matching pieces be inserted that are matched to the profile shape of the barstock and carry the seals.

In container 20 there is located an adapter insert 38. When viewed from outside, it has the shape of a cylinder. It fits in the inner volume of the jacket 22 and extends from the inner face of the one end wall 24 to the inner face of the other end wall 26. It has a recess that extends in the longitudinal direction 32 and is bounded transverse to the longitudinal direction by an inner wall 40. In the embodiment described, the adapter insert 38 has the same cross-section along the entire axial length thereof. The cross-section may however also taper from one end region of the adapter insert 38 to the other.

The section of the recess is matched to the section of the barstock 30. The various adapter inserts 38 differ in the shape of the recess, meaning in the orientation of the inner wall 40. Examples are given in the FIGS. 2 and 3.

As shown in FIG. 2, the cross-section of the recess substantially is a rectangle with rounded corners. A chamber or gap 42 is defined between the section of the barstock 30 and the inner wall 40 of the adapter insert 38. Said gap is also called "perimeter" gap because it completely surrounds the section of the barstock 30. Said gap 42 has a width in a direction transverse to the longitudinal direction 32. Said width of gap 42 changes as little as possible along the perimeter around the barstock 30. It is in any case chosen so as to allow for uniform fluid circulation around the section of the barstock. The chamber designates the volume defined by the inner wall.

It can be seen from these FIGS. that the adapter insert 38 has at least one recess 44 that extends outward, from the inner wall 40 to the outer wall thereof. Said recess is flush with a hole in the jacket 22 and receives an ultrasonic probe 46 that may be positioned in the longitudinal direction thereof. In the concrete embodiment shown, the ultrasonic probe is housed in a tube 48 that may be displaced in the recess 44 and the hole. The ultrasonic probe, which is connected to the tube, can thus be displaced in the direction of the axis of the tube 48. It may more specifically be completely removed from the container 20. It may be secured in any position within the recess 44, a suited holding device (not shown) being provided for this purpose between tube 48 and jacket 22. The tube also accommodates the electrical supply lines of the ultrasonic probe 46.

When an adapter insert 38 is replaced, the tube 48 is pulled outward until it disengages from recess 44. It then no longer hinders axial removal of the adapter insert 38. One end wall 24 is removed for this purpose.

In the adapter insert 38 there are further provided flow guide channels 50 for supplying and evacuating a coupling fluid 52 which, in operation, fills the gap 42 between inner wall 40 and barstock 30. In the embodiment shown there is provided one flow guide channel 50 for supplying said fluid and one flow guide channel 50 for evacuating the same. A plurality of flow guide channels for fluid supply and/or evacuation may also be provided.

In the exemplary embodiment shown, the flow guide channel 50 for supplying the coupling fluid 52 ends in a nozzle 54 in proximity to gap 42. Said nozzle is substantially disposed tangentially, meaning in a circumferential direction around gap 42, the reader being referred to arrow 56 that indicates the circumferential direction and symbolizes the flow of the coupling fluid 52 around barstock 30. The spiral flow around the barstock is achieved in that the coupling fluid 52 enters the nozzle 54 under pressure so that it is forced to flow in the circumferential direction shown by the arrow 56.

The nozzle 54 and, as a result thereof the inlet, are located in an axial end region of container 20. At the other axial end region there is located the flow guide channel 50 for evacuating the fluid. As shown in the exemplary embodiment, the flow guide channels 50 are laid so as to end at the end faces of the adapter insert 38. There, they are coupled through a plug coupling to lines 58 that are passed through the end walls 24 and 26 respectively and extend as a continuation thereof. The coupling fluid 52 is supplied or removed via said lines 58.

In a different embodiment, the lines are passed through the jacket 22.

Irrespective thereof, the lines 58 are arranged so that the lines 58 may remain in the same position with all of the possible adapter inserts 38 being used. The different adapter inserts 38 substantially only differ in the shape of their inner axial recess, meaning in the course of the inner wall 40. This is also the difference between FIG. 2 and FIG. 3. Whereas in FIG. 2 the barstock 30 to be inspected is substantially a flat stock material with a rectangular cross-section, the barstock 30 to be inspected has a square cross-section in FIG. 3. Accordingly, the recess in the adapter insert 38 is differently implemented. It also has an approximately square cross-section with rounded corners. Rounded corners are also provided in the embodiment according to FIG. 2. The desired flow around the stock is achieved by suitably shaping the section of the recess. As shown in FIG. 3, there are provided additional ribs 60 that protrude inward from the inner wall 40 into the chamber. They are inclined in the direction of the arrow 56 indicating the circumferential direction. They are disposed in the direction of said arrow 56, each behind an edge around which the fluid is flowing, and cause the flow to be pressed against the region located behind the trailing edge in a spoiler-like fashion.

Other means may be used for achieving a uniform flow around as much of the perimeter of the cross-section of the barstock 30 to be inspected as possible. Instead of the ribs 60, projections may be used which reduce the width of gap 42 at certain sites on the perimeter and so on.

Typically, there is not provided one ultrasonic probe only but a plurality of ultrasonic probes 46 are being utilized during a testing task. As different sections of the barstock 30 require different positioning, a larger number of holes is provided for the probes in the jacket 42. With every adapter insert 38 being used, each hole is not matched with a recess 44. It is not necessary to use all of the recesses 44 or holes for performing a testing task. Holes that are not used are simply closed with a suited closure plug.

In the embodiment according to FIG. 4, the outer wall of adapter insert 38 is spaced a distance from the inner surface of jacket 22 of container 20. An annular cylindrical cavity is thus obtained in which the fluid is allowed to flow in a circumferential direction shown by the arrow 62. The lines 58 are arranged so that this flow is enforced. The flow guide channels 50 are now arranged so that the outer perimeter flow is allowed to enter and exit the chamber in the direction indicated by arrow 62. It is thus possible to leave the lines 58 unchanged when the adapter inserts 38 are being replaced. The various adapter inserts are configured so that the fluid is caused to flow around them as desired in the chamber 42 in the direction indicated by arrow 56.

Finally, FIG. 5 shows an exemplary embodiment in which the shape of the chamber 42 is not modified by special adapter inserts 38 but in which at least the jacket 22 is replaced. Different jackets 22 are provided for different barstock materials 30. In practice, the adapter inserts of the exemplary embodiments discussed herein above are used in principle, but they are developed and configured in such a manner that they also ensure (together with the end walls) the sealing function which, in the previous exemplary embodiments, was performed by the jacket cooperating with the end walls.

In the implementation according to FIG. 5, the jacket 22, which may be configured like the various adapter inserts 38, but may also be formed from a metal sheet or another material having the same wall thickness all over, is sealingly and removably connected to the end walls 24, 26. Special end walls may be provided for every single jacket 22, but universally utilizable end walls that cooperate with various jackets may also be used. The configuration of the chamber is not affected thereby.

What is claimed is:

1. A testing device for the ultrasonic inspection of barstock material, said testing device comprising:
    a container a) having a chamber disposed therein in which chamber the ultrasonic inspection is carried out, b) being provided with at least one passage for the barstock material to be inspected and c) being comprised of at least one inlet and at least one outlet for a coupling fluid, whereby the inlet and the outlet are arranged for the coupling fluid being circulated around the barstock material in a direction transverse to the longitudinal direction of the barstock material and at least one ultrasonic probe that is pointed at the barstock material,
    wherein the chamber has a non round cross-section in a direction transverse to the longitudinal direction of the barstock material and the cross-section of the chamber is matched to the section of the barstock material in such a manner that a perimeter gap between barstock material and an inner wall of the chamber substantially maintains its width.

2. The testing device according to claim 1, wherein the perimeter width of the gap varies less than 3:1.

3. The testing device according to claim 1, wherein the chamber is defined by an adapter insert and wherein the adapter insert is replaceably disposed within the container.

4. The testing device according to claim 3, wherein a plurality of different adapter inserts is provided for different sections of the barstock material to be inspected.

5. The testing device according to claim 3, wherein the adapter insert has flow guide channels for supplying to, and evacuating from, the chamber the coupling fluid, said channels communicating with the at least one inlet or the at least one outlet respectively.

6. The testing device according to claim 3, wherein the container has a jacket and two end walls, at least one end wall is removably connected to the jacket and the adapter inserts can be replaced when the end wall is removed.

7. The testing device according to claim 3, wherein the adapter inserts have an outer wall, an adapter insert inserted in the container has an annular perimeter region between the outer wall thereof and an inner wall of the container which is left free and said region communicates with the annular perimeter gap and receives coupling fluid.

8. The testing device according to claim 1, wherein the at least one inlet is disposed within the container in such a manner that coupling fluid exiting therefrom has a tangential motion component.

9. The testing device according to claim 3, wherein the cross-section of the chamber is defined by curves, and has no angles whatsoever.

10. The testing device according to claim 1, wherein the coupling fluid is water.

11. The testing device according to claim 1, wherein the perimeter width of the gap varies less than 2:1.

* * * * *